United States Patent [19]

Nitzsche

[11] Patent Number: 5,190,050
[45] Date of Patent: Mar. 2, 1993

[54] TIP DEFLECTABLE STEERABLE CATHETER

[75] Inventor: Ray Nitzsche, Edison, N.J.

[73] Assignee: Electro-Catheter Corporation, Rahway, N.J.

[21] Appl. No.: 790,225

[22] Filed: Nov. 8, 1991

[51] Int. Cl.⁵ .............................................. A61M 25/00
[52] U.S. Cl. .................................... 128/772; 604/164
[58] Field of Search ............... 604/158, 159, 164, 169, 604/170; 128/772

[56] References Cited

U.S. PATENT DOCUMENTS

| | | | |
|---|---|---|---|
| 3,625,200 | 12/1971 | Muller | 128/772 |
| 3,854,473 | 12/1974 | Matsuo | 128/772 |
| 4,757,827 | 7/1988 | Buchbinder et al. | 128/772 |
| 4,830,023 | 5/1989 | de Toledo et al. | 128/772 |
| 4,886,067 | 12/1989 | Palermo | 128/772 |
| 4,940,062 | 7/1990 | Hampton et al. | 128/772 |
| 4,998,916 | 3/1991 | Hammerslag et al. | 128/772 |
| 5,060,660 | 10/1991 | Gambale et al. | 128/772 |

Primary Examiner—Paul J. Hirsch
Attorney, Agent, or Firm—Cohen, Pontani, Lieberman, Pavane

[57] ABSTRACT

A steerable catheter includes a handle and a catheter tube, the tip of which may be selectively curved by an operator. Three elongated, substantially flat planar shims are juxtaposed in sandwiched relation and mounted within the tip of the catheter tube for movement relative to one another remotely from the catheter handle. When one of the three shims slides relative to the other two, the catheter tube tip bends to attain a user-controlled curvature. A curvature controlling and locking mechanism in the handle permits the operator to readily and accurately effect separate coarse and fine adjustments to the curvature of the catheter tip.

21 Claims, 5 Drawing Sheets

TIP DEFLECTABLE STEERABLE CATHETER

BACKGROUND OF THE INVENTION

This invention generally relates to vascular catheters and, most particularly, to catheters that can be remotely guided or steered by selective deflection of the catheter distal end or tip.

Catheters have been in common use in medical practice for many years. They are often used, for example, to probe locations inside a body lumen which are otherwise unreachable without surgery. A catheter is first inserted into a major vein or artery, or other body lumen, which is near the surface of the patient's body. The catheter is then guided to the area of concern by further inserting it into the body lumen. As medical knowledge increases, more uses of catheters have been developed and these uses have become more complex so that the ability to accurately and selectively steer the distally-located tip of the catheter has become of extreme importance. For example, there is a need to use steerable catheters to apply electrical pulses and the like to various internal, electrically excitable body tissues, such as the heart. Similarly, there is also a need to measure electrical currents existing in various body tissues and organs, such as the heart.

In order to place the tip of the catheter in the correct location and position, it is necessary to curve the tip of the catheter so that the catheter's distal end or tip will travel into the proper branch of a vascular lumen as the catheter is inserted. After the tip has been so curved, it is also often desirable to rotate the catheter's tip while maintaining the catheter tip's curvature so that the tip can then approach and contact the tissue of interest. In addition, once the catheter's tip has contacted the tissue of interest, it is also important that the tip make firm contact with the tissue so that an electrical current can be reliably applied by the catheter's tip to the tissue. Finally, it is desirable to be able to maintain the curvature of the exact catheter's tip during the procedure with a locking mechanism yet still permit ready, reliable and complete straightening of the catheter's tip upon command. It is also important to enable the user to selectively attain smooth, steady and predictable angular rotation of the tip as the handle or proximal end of the catheter is correspondingly rotated.

In known catheters, when the distal, curved tip must be rotated after encountering an obstruction, rotation of the proximally-located handle does not result in an equal, corresponding rotation of the catheter's distal tip until some threshold angular force or torque has thus been applied to the catheter base. At this point, the catheter tip can suddenly and uncontrollably spin in a jolt of rotation which, at the very least, reduces the angular resolution that is required by studies of the type normally undertaken with these devices.

SUMMARY OF THE INVENTION

The steerable catheter of the present invention effectively solves all of the foregoing problems.

The present invention is directed to a catheter, the distal tip of which may be easily, reliably and remotely manipulated or bent and locked into position using an attached proximally-disposed handle. The catheter of the invention comprises three primary portions: the catheter handle, the catheter tube, and the tip of the catheter tube.

Within the tip of the hollow catheter tube, three flat, rigid shims are mounted, attached to one another and to the outer shell of the catheter tube only at the distal ends of the shims. The three shims form a sandwich made up of an upper side shim, a center shim and a lower side shim. The proximal end of the upper shim is attached to an upper pull cable that is attached in series to an elastic band that, in turn, is attached to an anchor pin fixedly located within the catheter handle. The proximal end of the lower shim is attached to a lower pull cable that is attached to the handle anchor pin. The proximal end of the center shim rests against the distal end of a guidewire spring extending within and along the catheter tube. The guidewire spring is mechanically connected to a longitudinally movable collar sleeve mounted on the body of the catheter handle. When the collar sleeve is selectively displaced, relative to the handle body, longitudinally toward the distal tip, the guidewire spring is likewise longitudinally displaced in the distal direction, carrying with it the center shim. The upper shim, attached to the center shim at their proximal ends also, advances longitudinally in the distal direction relative to the catheter handle body, thereby causing the series-connected elastic band to stretch. However, the nonflexible lower pull cable anchors the lower shim relative to the body of the catheter handle and prevents it from sliding longitudinally relative to the handle body. As a result, the tip of catheter tube is caused to curve laterally downward in a plane perpendicular to the planes of the shim sandwich. The tight juxtaposition of the three relatively rigid shims ensures that the catheter tip will always curve in the same manner, and furthermore that this precise curve will remain stable even when external forces are applied to the catheter tip.

The catheter tube is hollow, containing within its central lumen the guidewire spring. The outer shell of the catheter tube is preferably formed of a relatively rigid material, preferably with a wire braid embedded therein. An unreinforced section of catheter tubing is fixedly attached to the distal end of the reinforced tube so as to form the selectively deflectable tip portion. The structure of the catheter tube and of the enclosed guidewire spring render the catheter tube sufficiently rigid so as to reliably transmit the longitudinal movement of the collar sleeve of the catheter's handle to the center shim in the catheter tube's tip. Its relative rigidity further assures insertion of the catheter tube into a patient without any possibility that the catheter tube will buckle.

A curve or deflection that is selectively formed at or proximate the distal tip of the catheter can be easily and reliably locked in position by the locking mechanism in the catheter's handle. When the collar sleeve of the catheter handle is translated longitudinally along the handle in the distal direction, a toothed lever mounted on the collar sleeve advances from one ratchet thread, cut into the body of the catheter handle, to the next ratchet thread where it is locked in place by the toothed lever which is urged into engagement with the thread by a resilient O-ring. To effectuate fine adjustment of the curvature of the catheter's tip, the collar sleeve is rotated relative to the handle body so that the toothed lever slides along grooves of the ratchet threads which have one or more helical grooves. In a preferred form of the inventive catheter handle, these threads are implemented as a single, continuous thread that extends helically about and along the handle. To reset and straighten the catheter tip, the toothed lever is depressed against the urgency of the resilient O-ring, thereby disengaging the lever's tooth from the ratchet thread. The series-connected elastic band acting upon the upper shim causes the three shims to return to their untensioned, flat planar straight positions, thereby straightening the catheter tip as collar sleeve on the catheter handle is longitudinally displaced in the proximal direction to its initial starting position. The tension provided by the elastic band ensures that the catheter's distal tip portion reliably returns to its initial straight shape after the curve locking mechanism in the catheter handle is disengaged, thereby substantially eliminating hysteresis in the return of the catheter's tip portion to its original, non-deflected condition.

Furthermore, the planar, flat shape of the three shims, combined with their relatively rigid construction and tight juxtaposition, ensure that the catheter's tip portion bends in only one orientation i.e. perpendicular to the planes of the shims.

The entire catheter tube can be easily and reliably rotated along its longitudinal axis by rotating the catheter handle body about its longitudinal axis. The construction of the catheter tube, comprising its relatively rigid outer shell, its embedded wire braid, and its guide-wire spring, ensure that an axial rotation of the catheter handle reliably translates to an equal and gradually-effected axial rotation of the catheter tube's tip portion. In addition, the shim construction permits the entire tip portion to be rotated while still maintaining the exact user-selected curvature of the tip portion. Also the structure of the catheter of the present invention allows the catheter's tip portion to be pressed tightly against a patient's internal tissues by simply applying an appropriate longitudinal or rotative force to the catheter handle, even when the tip portion has been and remains curved. This ability to accurately translate a longitudinally applied force is enabled at least in part by the strength of the catheter tube structure in combination with the three juxtaposed flat shim design.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

DETAILED DESCRIPTION OF THE INVENTION

Figure 1:
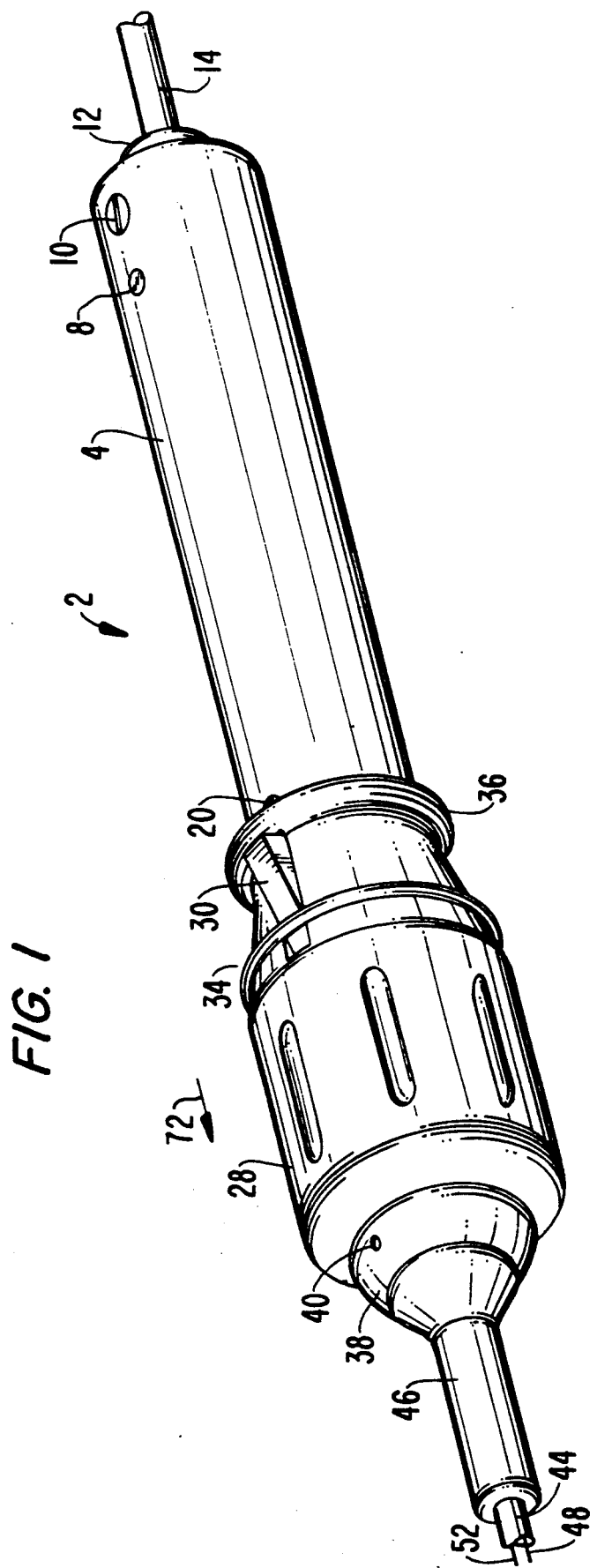
FIG. 1 is an elevated perspective view of the handle portion of a preferred embodiment of the steerable catheter of the present invention.
Figure 2:
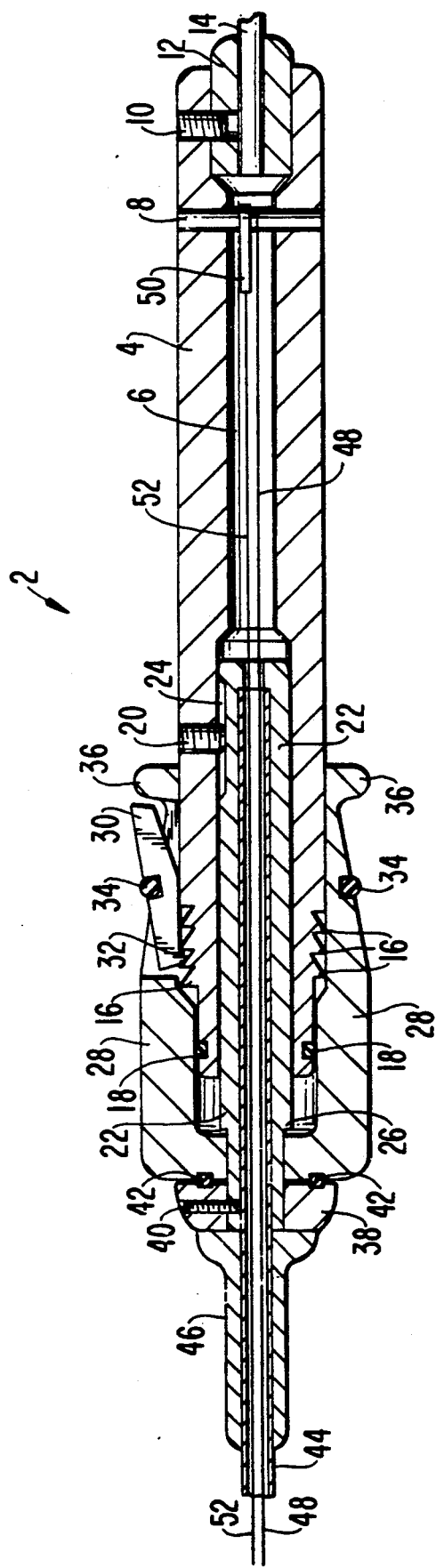
FIG. 2 is longitudinal cross-sectional view of the handle portion of a preferred embodiment of the steerable catheter of the present invention.

FIGS. 1 and 2 depict a preferred embodiment of the steerable catheter of the present invention. The handle 2 of the catheter is comprised at its proximal end of a generally cylindrical body 4 having a central lumen 6 that extends longitudinally through and along the entire length of body 4. At the proximal end of body 4 are two lateral bores or holes. The first hole passes entirely through body 4 from its upper surface, through central lumen 6, to its lower outer surface. Within this hole an anchor pin 8 is securely mounted. The second hole passes from the outer surface of body 4 to central lumen 6 of body 4. A set screw 10 is threadedly mounted in this second hole and functions to engage and securely mount a plug 12 within the near most end of the central lumen 6 of body 4. Plug 12 includes an aperture with which set screw 10 engages. Plug 12 also has a longitudinally oriented central lumen into which an end tube 14, also provided with a central lumen, is securely mounted. Body 4 is threaded proximate its forward (i.e. leftward in the figures) near its distal end with one or more helical ratchet threads 16 which circumscribe and corkscrew longitudinally along the outer surface of body 4. At the forward most end of body 4 is a circumferential groove into which is fitted an O-ring 18 which is comprised of a resilient material, such as rubber. Near the longitudinal center of body 4 is a third lateral bore or hole into which is threadedly mounted a set screw 20. The hole in which set screw 20 is received passes from the outer surface of body 4 to the central lumen 6 of body 4. Base cylinder 22 is slidably mounted within the distal portion of the central lumen 6 of body 4 so that a portion of base cylinder 22 extends beyond the distal end of body 4.

A base cylinder 22 has a longitudinal central lumen that extends along its entire length and a longitudinal notch 24 at its rearward end. Base cylinder 22 is positioned within central lumen 6 of body 4 so that set screw 20 engages and slides within the notch 24, and set screw 20 is of sufficient length and is screwed sufficiently deeply into body 4 so as to extend into notch 24. The forward end portion of base cylinder 22 is narrowed, forming a circumferential flange 26, and there is a lateral bore or hole defined in the forward, narrowed end of base cylinder 22 and passing from its outer surface to its central lumen.

A collar sleeve 28 is rotatably mounted onto the narrowed forward end of base cylinder 22 so that collar sleeve abuts flange 26 of base cylinder 22. Collar sleeve 28 is roughly cylindrical in shape with a central, longitudinally oriented lumen. As shown in FIG. 2, collar sleeve 28 and its central lumen are shaped so that the collar sleeve 28 surrounds a portion of the forward end of base cylinder 22 and the forward end of body 4, including ratchet threads 16. A longitudinal slot is cut through collar sleeve 28, into which slot is mounted an engagement lever 30. Lever 30 has a tooth 32 at its forward end for engagement with a ratchet thread 16 of the body 4. Although lever 30 is shown as having a single tooth 32 that engages a single thread 16, the lever 30 may alternatively have more than one tooth 32 for concurrent engagement with more than one thread or thread portion 16. Lever 30 further has a lateral groove which is aligned with a circumferential groove in collar sleeve 28 and into which is mounted on O-ring 34 formed of a suitably resilient material such as rubber.

Lever 30 is shaped so that it defines a fulcrum portion in its lower surface for contact with an outer surface portion of the body 4. The lateral groove in lever 30 is positioned forwardly from the fulcrum portion of lever 30 so that O-ring 34 normally urges tooth 32 into engagement with a ratchet thread 16. As shown in FIG. 2, the ratchet threads 16 have rearward edges that slope at an angle of about 30° from the axis of central lumen 6 and forward edges that slope at an angle of about 90° so that the points of the ratchet threads 16 are about 60° in cross-section. However, in a more preferred embodiment the tooth 32 of lever 30 will engage with enhanced reliability when the points of the ratchet threads protrude forwardly, i.e. so that the rearward proximal edges of the ratchet thread 16 slope at about 30°, the forward edges at about 94°, each with respect to the central lumen axis, and the points of the ratchet threads 16 are about 56° in cross-section. The shape of the tooth 32 of lever 30 may also be appropriately modified for enhanced latching engagement with the threads 16. The rearward end of the collar sleeve 28 terminates in a flange portion 36.

Also mounted onto the narrowed forward end of base cylinder 22 is an end collar 38 which is roughly annular in shape. End collar 38 has a lateral bore or hole into which is mounted a set screw 40 that passes through end collar 38 into the hole at the distal end of base cylinder 22 to thereby secure and removably mount the end collar 38 to the base cylinder 22. Collar sleeve 28 and end collar 38 each have a respectively aligned annular groove in their abutting surfaces and into which is fitted an O-ring 42 formed of a resilient material such as rubber.

A catheter tube 44 fits into the forward end of the central lumen of base cylinder 22 and is secured therein by the set screw 40 which engages the outer surface of catheter tube 44. Tube 44 has a central lumen and is described in more detail below with particular reference to FIGS. 4, 5 and 6. Strain relief end 46 is fastened to catheter tube 44, as by an adhesive bond or the like, so that when catheter tube 44 is fully inserted and fixed within base cylinder 22, the strain relief end 46 contacts end collar 38. Strain relief end 46 is intended to minimize the effect upon handle 2 and its constituent elements of any flexing of the proximal end of catheter tube 44 during use of the catheter of the present invention and, in addition, provides a liquid-tight seal between the catheter tube periphery and the interior of the catheter handle assembly.

Within central lumen 6 of body 4, one end of a first or lower pull cable 48 is securely wound around or otherwise attached to anchor pin 8, while the other or opposite end of the lower pull cable 48 passes through and along the central lumen of catheter tube 44 to its tip portion 54, shown in FIGS. 3, 4, 5 and 6. One end of an elastic band 50 is also mounted about the anchor pin 8 while the other end of the elastic band is attached, so as to form a series connection, to a second or upper pull cable 52 which passes through the central lumen of catheter tube 44 to its tip portion 54, as shown in FIGS. 3, 4, 5 and 6. Lower pull cable 48 and upper pull cable 52 are comprised of a material that is substantially or effectively nonstretchable when pulled longitudinally—such, for example, as the presently preferred stainless steel 302, with a gauge of about 0.009. Elastic band 50 is comprised of a material that stretches but which also has an elastic memory so that once a stretching force is removed, the elastic band returns to its original, substantially unstretched condition. Alternatively, elastic band 50 may be replaced by a spring or other suitably resilient means.

Figure 3:
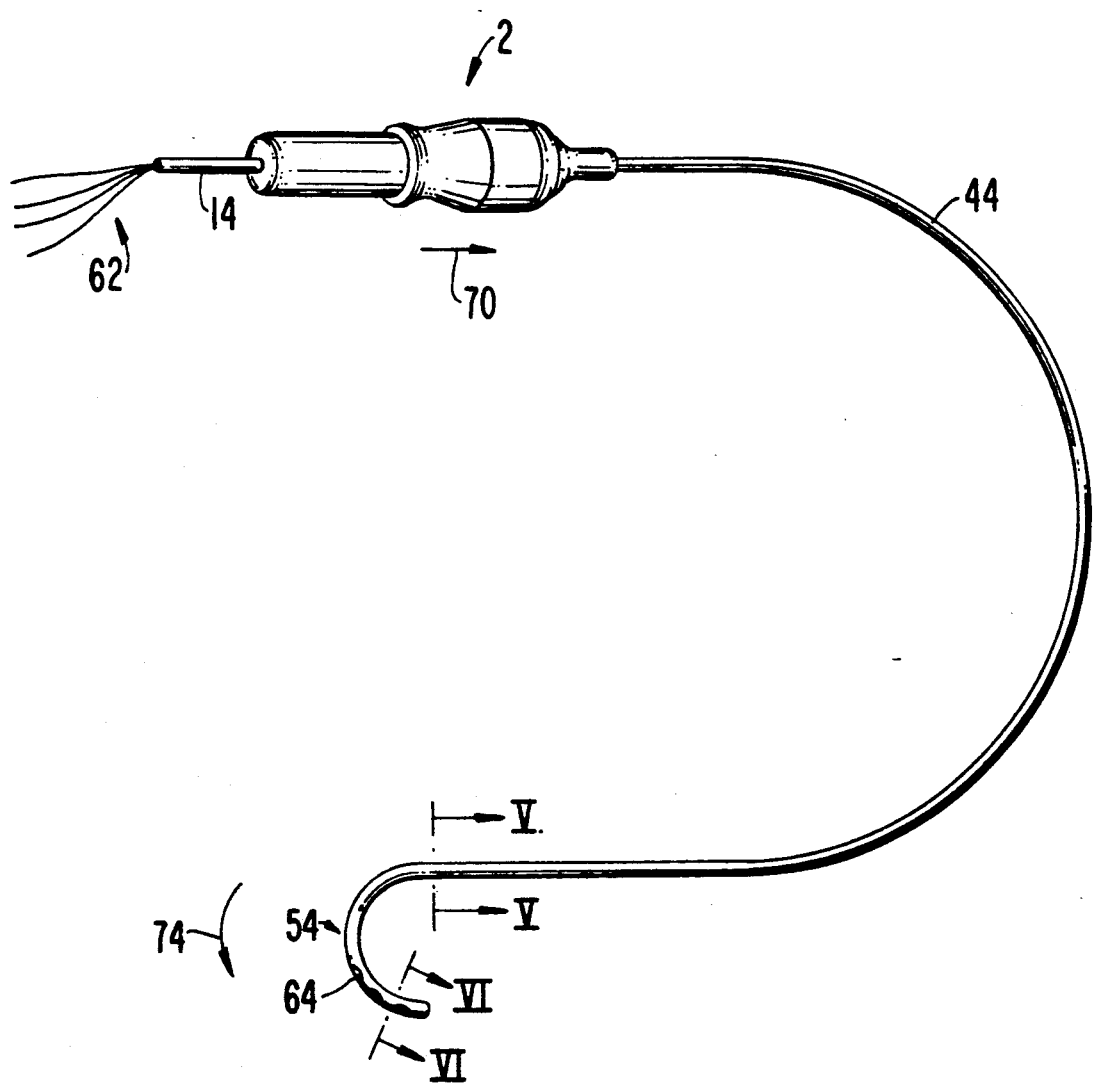
FIG. 3 is a simplified perspective drawing of a preferred embodiment of the steerable catheter of the present invention.

Referring now to FIG. 3, catheter tube 44 has a length sufficient for it to be inserted through a patient's skin or body orifice and into a blood vessel or other body lumen or cavity or the like so that tip portion 54 of catheter tube 44 can be controllably directed and reach a particular point or location within the patient's body—for example a location within the vascular system, such as the heart.

Figure 4:
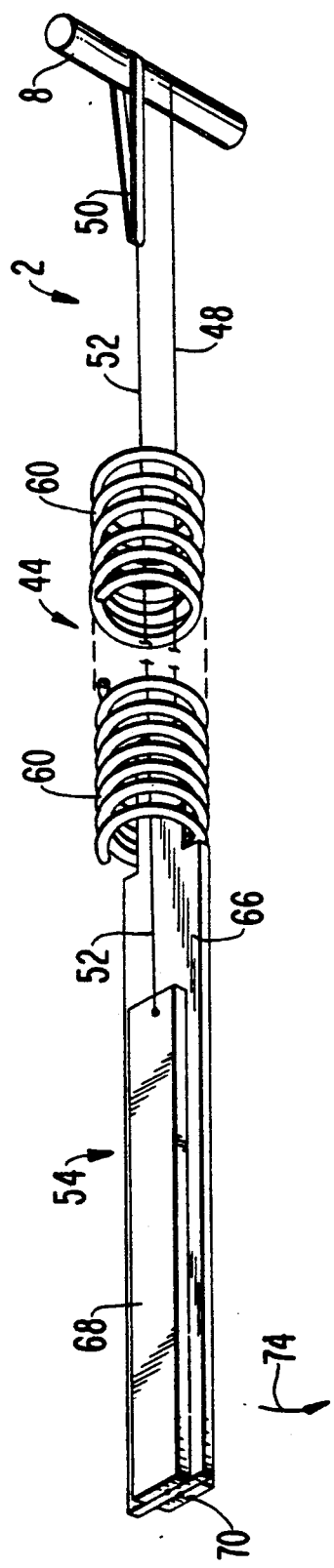
FIG. 4 is a simplified perspective drawing of the distally-located tip deflection mechanism, with the outer sleeve removed, of a preferred embodiment of the steerable catheter of the present invention.
Figure 5:
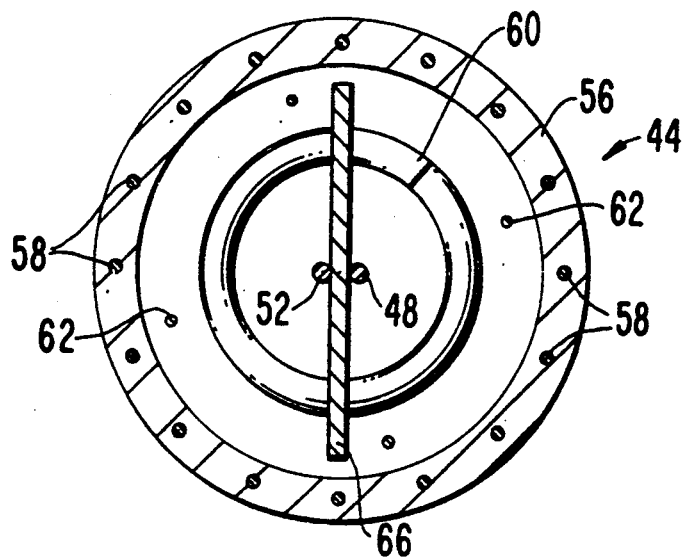
FIG. 5 is a cross-sectional view of the catheter tube taken along the lines V—V in FIGS. 3 and 4.
Figure 6:
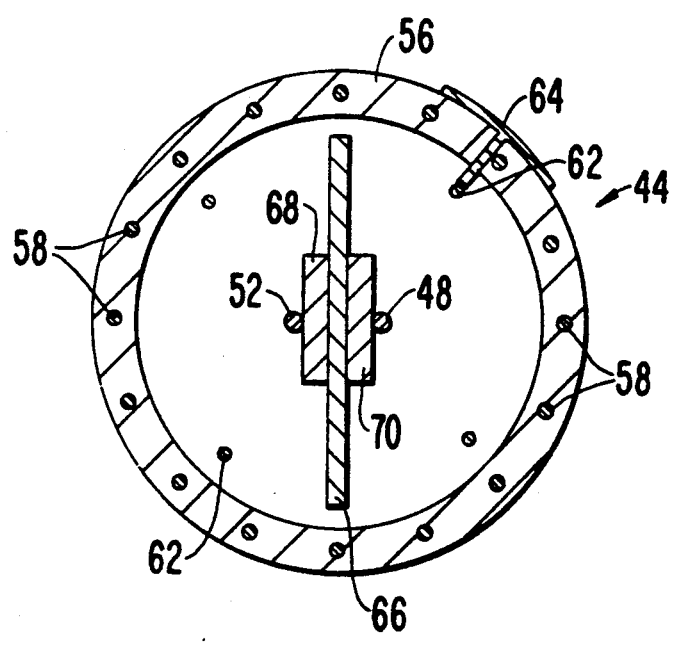
FIG. 6 is a cross-sectional view of the catheter tube taken along the lines VI—VI in FIG. 4.

Referring particularly to FIGS. 4, 5 and 6, catheter tube 44 is partially comprised of a hollow outer shell 56 which is formed of a rigid material, preferably a nylon coat polymer such as "Pebax" resin, manufactured by ATOChem. In order to give the outer shell 56 of catheter tube 44 substantial effective rigidity and strength, a wire braid 58 is embedded into the outer shell. Wire braid 58 is preferably comprised of about 16 steel wires that are interwoven along the length of catheter tube 44. Wire braid 58 may, alternatively, be comprised of more or less than 16 wires and the wires may, alternatively, be comprised of a material other than steel such, illustratively, as fiberglass. The nylon coat polymer and wire braid 58 strengthen and support the structure of catheter tube 44 in the same way as concrete and embedded metal reinforcement rods or bars, respectively, are used in building construction.

Disposed radially within the central lumen of outer shell 56 of the catheter tube 44 is a guidewire spring 60 which provides columnar strength to the catheter tube. The size of guidewire spring 60 is so selected that its outer diameter is slightly less than the inner diameter of outer shell 56; in one currently preferred embodiment, the outer diameter of guidewire spring 60 is about 0.038 inches while the inner diameter of outer shell 56 is about 0.056 inches. Guidewire spring 60 is implemented as a long, tightly wound spring and is disposed within and along almost the entire length of catheter tube 44, extending from the rearward end of base cylinder 22 to almost the rearward or proximal end of the tip portion 54 of catheter tube 44. A plurality of insulated electrical wire conductors 62 are disposed in the annular space defined between the outer shell 56 and guidewire spring 60. The electrical conductors 62 may, for example, have peripheral coatings that electrically insulate the electrical conductors 62 one from another and from the spring 60. One end of each of the electrical conductors 62 passes to a respective electrical contact plate 64 that is integrally carried on the outer surface of the outer shell 56 at or along the tip portion 54 of catheter tube 44. One electrical contact plate 64 is preferably disposed at the distal most end of the tip portion 54 of catheter tube 44 as shown in FIG. 3. The electrical conductors 62 pass through the entire length of catheter tube 44, through the central lumen in handle 2, and through and out of end tube 14 where they may be separately connected to signal sensors or to an electrical power source (not shown) which can selectively provide electrical pulses or signals to one or more of the conductors 62. The outer shell 56 of tip portion 54 of catheter tube 44 is preferably formed of substantially the relatively rigid material, as for example of the same resin family, as is the outer shell of the non-tip portion of catheter tube 44; however, the outer shell 56 of tip portion 54 may, alternatively, be comprised of a lower durometer or "softer" material to increase its flexibility, so long as such material admits of firm attachment of the tip portion to the distal end of the proximally-disposed reinforced remainder of the catheter tube shell. In addition, it is preferred that the outer shell 56 of the tip portion 54 not include an interior wire braid, thereby facilitating its selective bendability under a user's control and permitting the incorporation of the electrode pads 64.

Referring now to FIGS. 4 and 5, the distal end of guidewire spring 60 contacts the elongated, rearward or proximal end portion of a center shim 66 which is disposed longitudinally within tip portion 54 of catheter tube 44. Center shim 66 is formed as an elongated, flat plate and has a transverse width approximately equal to or greater than the outer diameter of guidewire spring 60, preferably about 0.044 inches in width. Center shim 66 preferably has a reduced width portion at its rearward end that extends for a short distance into the central lumen of guidewire spring 60 and defines a pair flanges on opposite sides of the reduced width portion for abutment with the distal end of the spring 60. The guidewire spring thus provides a seat for the center shim 66. Alternatively, the proximal end of center shim 66 can be securely fastened, as by soldering, to the distal end of the guidewire spring 60. An upper shim 68 and a lower shim 70 are juxtaposed on opposite faces of the center shim 66, thereby forming a sandwich-like construction with the center shim 66 between the two outer shims. Each of the shims 68 and 70 is also formed as an elongated, flat plate. Due to the concave curvature of the interior periphery of the outer shell 56, each of upper shim 68 and lower shim 70 has a width less than that of the center shim 66, preferably a width of about 0.020 inches. Shims 66, 68 and 70 are all relatively thin and comprised of a material that is relatively rigid, such as stainless steel with a thickness of about 0.004 to 0.005 inches. Where the catheter includes electrical signal sensing and/or applying pads or plates 64 or the like in the tip portion 54, each of the shims 66, 68, 70 may, as appropriate, be electrically insulated—such for example by an insulative external surface coating—so as to prevent shorting to solder joints and the like.

The distal or forward end of the upper pull cable 52 is securely fastened, as by soldering, to the rearward or proximal end of the upper shim 68. Similarly, the distal end of the lower pull cable 48 is securely fastened, as by soldering, to the proximal end of the lower shim 70. The forward or distal end of the center shim 66 is securely fastened, as by soldering, to the distal end of each of the side shims 68 and 70. Furthermore, the distal end of the tip portion 54 may be sealed with the material that forms the outer shell 56 of tip portion 54 to enclose the distal ends of shims 66, 68 and 70 and thereby connect the shim distal ends to the distal end of tip portion 54.

In operation, the tip portion 54 of catheter tube 44 is first inserted into, for example, a patient's vessel such as a blood vessel or the urethra. The location of the tip portion 54 within the patient is typically monitored noninvasively as, for example, through the use of X-rays or sonography or the like. When the tip portion 54 of catheter tube 44 reaches a point in the body or vessel at which the tip portion must be precisely steered or directed, as at a point where two vessels meet or within a heart chamber, the tip portion 54 can be selectively caused to assume a curved or bent shape, as shown in FIG. 3, from its normally straight, generally linear disposition by the doctor or operator through activation of the catheter tip deflector control mechanism in handle 2. To do this, the operator holds the rearward portion of handle body 4 in one hand and, with his thumb, slowly pushes the flange portion 36 of collar sleeve 28 in the distal direction, i.e., in the direction of arrow 72 in FIGS. 1 and 2. As a result, collar sleeve 28 longitudinally slides and is displaced distally, together with end collar 38, base cylinder 22 and the guidewire spring 60 of catheter tube 44, all relative to the body 4. The distal movement of guidewire spring 60 effects likewise distal displacement of the center shim 66 within the tip portion 54 of catheter tube 44. The distal advancement of center shim 66 is translated, through its connection to the outer or side shims, to the distal ends of upper shim 68 and lower shim 70 which also attempt to advance distally therewith. The presence of the elastic band 50 in series connection with the upper pull cable 52 fully permits this longitudinally shifting or displacement of the upper shim 60 with the center shim 66, with the band 50 elastically stretching to accommodate the increased distance between the upper shim distal end and the anchor pin 8. However, the substantially non-stretchable lower pull cable 48 that extends between the rearward end of lower shim 70 and the post 8 that is anchored to the handle body 4 prevents any effective increase in the distance therebetween as the collar sleeve 28 is distally advanced. Because the lower shim 70 is therefore unable to move distally relative to the body 4, the lower shim is caused to longitudinally bend in accordance with the amount of distal displacement applied to the collar sleeve 28. The sandwiched construction of the shims 66, 68, 70 correspondingly causes the tip portion 54 of catheter tube 44 to likewise bend laterally downward, in the direction of arrow 74 in FIGS. 3 and 4, and thereby assume a curved configuration such as that shown in FIG. 3.

As collar sleeve 28 is displaced distally along the body 4 of handle 2, the tooth 32 of lever 30 rides up the rearward wall or face and thereby slips out of one ratchet thread 16 and into the next distally succeeding ratchet thread. The resilience of O-ring 34 permits pivoted movement of the lever 30 and then urges its tooth 32 to ride down into and latch to this next succeeding ratchet thread 16 through its return urgency. As a result of this successive slipping and latching action, tooth 32 of lever 30 automatically locks the collar sleeve 28 in its distally displaced position even when the operator removes thumb pressure from the collar sleeve flange portion 36, thereby also locking and preserving the curve substantially attained in the tip portion 54 of catheter tube 44. By thus advancing the collar sleeve 28 in the distal direction, coarse adjustment of the curvature of tip portion 54 of the catheter tube is effected. To then attain a finer adjustment in the tip portion curvature, the operator rotates the collar sleeve 28 about its longitudinal axis of rotation (which coincides with the central lumen 6 of body 4) relative to the handle body. As a result of this rotation of the collar sleeve 28, the tooth 32 of lever 30 rides along the helical ratchet thread 16 of body 4 effecting gradual, continuous and relatively minute longitudinal translation of collar sleeve 28 in the distally-advancing direction of arrow 72 or, alternatively for opposite sense rotation of the sleeve 28, in the proximally-withdrawing direction opposite that indicated by arrow 72, as appropriate or desired.

To thereafter rapidly straighten the tip portion 54 of catheter tube 44, lever 30 is depressed proximate its rearward end causing lever 30 to pivot on its fulcrum portion, thereby disengaging tooth 32 from ratchet thread 16. The return urgency or tension provided by elastic band 50 with respect to collar sleeve 28 (through pull cable 52, upper shim 68, distally attached center shim 66, guidewire spring 60, base cylinder 22 and end collar 38) automatically causes, in response to the disengagement of tooth 32 from ratchet thread 16, return displacement of collar sleeve 28 in the rearward or proximal direction, i.e. in the direction opposite that indicated by arrow 72, thereby rapidly straightening tip portion 54 of catheter tube 44 to its initial straight shape. Alternatively, the tip portion 54 can be straightened slowly by rotating collar sleeve 28 in the appropriate direction, or by pivoting the lever 30 while grasping the sleeve 28 so as to permit its rearward return displacement in a selectively gradual manner. The tension provided by elastic band 50 ensures that the tip portion 54 fully returns to its initial, straight condition once the curve locking mechanism is partially or wholly disengaged, at the same time minimizing or eliminating hysteresis in this return motion of the deflected or curved catheter tip. It should also be recognized that the inventive catheter can be provided with the capability of selectively curving the tip portion bidirectionally by predeterminately adjusting the length of the elastic band and/or nonstretchable pull cable(s) so that, in the initial or neutral or nondisplaced condition of the handle body and collar sleeve, the catheter tip portion is maximally bent in one direction, thus requiring a first distally-oriented relative displacement of the collar sleeve to bring the tip portion to its straight or uncurved condition and a second or further distally-oriented relative displacement of the collar sleeve to curve the tip portion in the opposite direction.

As a consequence of the planar, flat shape of the shims 66, 68 and 70, the relatively rigid material of which they are formed, and the tightly sandwiched juxtaposition of the shims, it is virtually impossible for the tip portion 54 to bend in normal use in any direction other than substantially perpendicular or lateral to the planes of the shim 66, 68 and 70, as for example the direction indicated by arrow 74. The sandwiched shim design also makes it virtually impossible for the tip portion 54 to bend out of the plane of its curvature once a curve has been locked into place by the latching mechanism of the present invention.

In use, it is often desirable to selectively rotate the entire catheter tube 44 through a desired angular adjustment after a curve in tip portion 54 has been attained and locked in place. Such a rotation may be readily and reliably achieved by selectively rotating the entire handle 2, through manipulation of the handle body 4 together with collar sleeve 28, about its longitudinal axis. The preferred rigidity and stability of the material and structure comprising the outer shell 56 of catheter tube 44 and the supporting structure of the guide spring 60 allow such axial rotation of the handle 2 to be smoothly, directly and reliably transmitted to the tip portion 54 of catheter tube 44 without any unintended or unanticipated sudden rotational movements or jolts. Thus, a given axial rotation of handle 2 will result in a corresponding, equal axial rotation of catheter tube 44 and a corresponding, equal rotation of its tip portion 54 while maintaining the latched curvature of tip portion 54. Gradual axial rotations of the tip portion 54 of up to or exceeding 360° can therefore be reliably achieved without sensitivity to rotational position through simple rotation of handle 2. Furthermore, the relatively rigid material forming the three shims and their flat, sandwiched juxtaposition are also effective to ensure reliable, steady rotation of the entire tip portion 54 without any sudden jolts of rotation while, at the same time, maintaining the locked curvature of the tip portion 54.

Finally, it should be recognized that the rigidity of the material and structure of the catheter tube 44 and shims 66, 68 and 70 allow the tube 44 to be strenuously urged longitudinally in the distal direction indicated by arrow 72 so as to firmly and aggressively press against and contact particular tissue within a patient's body, such as heart tissue, without risk that the catheter tube 44 or its tip portion 54 will buckle or unexpectedly deform.

As will be appreciated from the foregoing description, the longitudinally-oriented length of the notch 24 is selected so that the set screw 20 limits the longitudinal movement of base cylinder 22 (and therefore of collar sleeve 28 along the body 4), thereby also defining the bounds or limitations of curvature of the tip portion 54 of catheter tube 44. O-ring 18 ensures that body 4 slides uniformly and tightly through the center lumen of collar sleeve 28. O-ring 42 allows the end collar 38 to slide easily with and against the collar sleeve 28.

In addition, the use of set screws 10, 20 and 40, of O-ring 34 and of anchor pin 8 permits the handle to be readily assembled and disassembled for cleaning, adjustment or repairs.

Thus, while there have been shown and described and pointed out fundamental novel features of the invention as applied to a preferred embodiment thereof, it will be understood that various omissions and substitutions and changes in the form and details of the disclosed apparatus, and in its operation, may be made by those skilled in the art without departing from the spirit of the invention. It is the intention, therefore, to be limited only as indicated by the scope of the claims appended hereto.

Illustratively, although the steerable catheter of the present invention has been described as having three shims, in an alternative embodiment, only two shims may be used in the tip portion 54 of catheter tube 44. In this modified form of the inventive catheter, upper shim 68 is eliminated and upper pull cable 52 may, instead, be attached to the rearward or proximal end of the center shim 66. The two-shim catheter of this modified embodiment operates in substantially the same way as the illustrated three-shim catheter except that center shim 66, being attached through upper pull cable 52 to the series-connected elastic band 50, provides the force both to restore the tip portion 54 of catheter tube 44 to its initial straight shape and to urge the catheter tube 44 and collar sleeve 28 in the longitudinally rearward direction, i.e. in the direction opposite arrow 72.

Additionally, although the steerable catheter of the present invention is expressly disclosed for use in sensing electrical signals in body tissues and applying electric power to such tissues, the catheter design may be readily and suitably modified for use in the pumping of fluids (liquid or gas) into or out of a patient. In such an alternate embodiment, the electrical contact plates 64 in the catheter's tip portion 54, the electrical conductors 62 and the electrical power source may be eliminated. Instead, one or a plurality of holes or apertures are provided in the catheter's tip portion 54, and an appropriate pump or the like is connected to rearward end tube 14 so as to provide suction to evacuate fluid from the patient or to positively pump fluid and/or medications into the patient. Similarly, optical fibers can be provided instead of, or in addition to, electrical conductors 62. In such an embodiment one or more optical fibers may be connected to a light source, such as a laser, while one or more other optical fibers are connected to a video camera and/or similar viewing or recording devices. Alternatively, a longitudinally movable rigid cable may protrude through a bore or opening in the catheter's tip portion 54 for removal of patient tissue for biopsy. Any one or more of these alternative embodiments may also be combined one with another for a particular use contemplated or intended for the tipdeflatable, steerable catheter of the present invention. Finally, and as should be apparent to those skilled in the art, the dimensions herein mentioned relate to one particular catheter size in the particular embodiment of the inventive apparatus shown in the drawings and are disclosed solely by way of example and should not, therefore, be understood as an intended limitation on the scope of the invention.

What is claimed is:

1. A tip-deflectable, steerable catheter comprising:
   a catheter handle having a body and a collar sleeve, said collar sleeve being slidably mounted onto and for selective longitudinal sliding movement relative to said body;
   an elongated catheter tube having longitudinally spaced apart proximate and distal ends, said proximal end of said catheter tube being fixedly attached to said collar sleeve of said catheter handle;
   a catheter tip portion carried at said distal end of the catheter tube and having a distal end most remote from said handle;
   an elongated, substantially flat planar first shim having longitudinally spaced apart proximal and distal ends and disposed within said catheter tip portion, said first shim distal end being attached to said catheter tip portion proximate said tip portion distal end, and said first shim proximal end being attached and anchored to said catheter handle body; and
   an elongated, substantially flat planar second shim having longitudinally spaced apart proximal and distal ends and disposed within said catheter tip portion in face-to-face overlying abutment with said first shim, said second shim distal end being attached to said first shim distal end and said second shim proximal end abutting said distal end of the catheter tube so that longitudinal movement of said catheter tube distal end as said collar sleeve is selectively moved longitudinally toward said catheter tip portion relative to said handle body causes said proximal end of said second shim to move correspondingly longitudinally and said attachment of said first shim to said catheter handle body causes tip-deflecting curvature of said catheter tip portion in accordance with said selective longitudinal movement of said collar sleeve.

2. The steerable catheter of claim 1, further comprising curvature locking means on said handle and operable for locking said catheter tip portion into a selected curvature.

3. The steerable catheter of claim 1, wherein:
   said catheter tube includes a central lumen defined in and extending longitudinally from said proximal end to said distal end of said catheter tube;
   said catheter tip portion includes a central lumen defined in and extending longitudinally along said tip portion, said central lumen of said catheter tip portion being aligned with and connected to said central lumen of said catheter tube; and
   said first and second shims being disposed within said central lumen of said catheter tip portion.

4. The steerable catheter of claim 3, further comprising a first pull cable attaching said first shim to said catheter handle body, said first pull cable extending slidably within and along the central lumen of said catheter tube.

5. The steerable catheter of claim 1, further comprising:
   an elongated, substantially flat planar third shim having longitudinally spaced apart proximal and distal ends and disposed within said catheter tip portion in face-to-face overlying abutment with said second shim and with said second shim being sandwiched between said first and third shims, said third shim distal end being attached to said distal ends of said first and second shims; and
   resilient means attaching said third shim proximal end to said catheter handle body.

6. The steerable catheter of claim 5, further comprising curvature locking means on said handle and operable for locking said catheter tip portion into a selected curvature.

7. The steerable catheter of claim 5, wherein:
   said catheter tube includes a central lumen defined in and extending longitudinally from said proximate end to said distal end of said catheter tube;
   said catheter tip portion includes a central lumen defined in and extending longitudinally along said tip portion, said central lumen of said catheter tip portion being aligned with and connected to said central lumen of said catheter tube; and
   said first, second and third shims being disposed within said central lumen of said catheter tip portion.

8. The steerable catheter of claim 7, further comprising a first pull cable attaching said first shim to said catheter handle body, said first pull cable extending slidably within and along the central lumen of said catheter tube.

9. The steerable catheter of claim 8, wherein said resilient means attaching said third shim to said catheter handle body comprises:
   a second, substantially nonstretchable pull cable having longitudinally spaced apart proximal and distal ends, said second pull cable distal end being fixedly attached to said third shim proximate said third shim proximal end; and
   an elastic member connected joiningly between said second pull cable proximal end and said catheter handle body.

10. The steerable catheter of claim 9, further comprising curvature locking means on said handle and operable for locking said catheter tip portion into a selected curvature.

11. The steerable catheter of claim 10, wherein said curvature locking means comprises:
   a latching thread on said handle body;
   a member carrying a tooth for releasable engagement with said latching thread; and
   means attaching said member to said collar sleeve for pivotal movement of said member between a first position in which said tooth engages said latching thread and a second position in which said tooth is disposed out of engagement with said thread, and normally biasing said member into said first position.

12. The steerable catheter of claim 11, wherein said member comprises a pivotally disposed, elongated locking lever, and said tooth is carried proximate one end of said lever.

13. The steerable catheter of claim 12, wherein said handle body is elongated and said latching thread comprises a helical thread oriented substantially transverse to the elongation of said handle body.

14. The steerable catheter of claim 13, wherein said means comprises a resilient member connecting said locking lever to said collar sleeve at a substantially central portion along the elongation of said lever.

15. A catheter handle operable for selective user-manipulated control of the curvature of a deflectable tip portion of a steerable catheter and for releasably locking the tip portion of the steerable catheter into a selectively defined curvature, said curvature of the catheter tip portion being effected by first and second mechanical couplings such that the tip portion assumes a user-selected curvature when the second mechanical coupling is moved longitudinally from an initial position relative to the first mechanical coupling, said catheter handle comprising:
  a user-graspable body having longitudinally spaced apart proximal and distal ends, the first mechanical coupling being attached to said body;
  a user-manipulatable collar sleeve disposed on and for longitudinal sliding movement relatively along said body, the second mechanical coupling being attached to said collar sleeve so that as said collar sleeve is longitudinally moved relative to said body the curvature of the catheter tip portion is varied in accordance with said relative longitudinal movement; and
  locking means on at least one of said body and collar sleeve for releasably locking said collar sleeve in a selected, user-manipulated position relative to said body and thereby locking the catheter tip portion in a user-selected and user-controlled curvature;
  said locking means comprising cooperating means on said body and on said collar sleeve for enabling user-selected gross and fine operating modes for user-controlled adjustment of the curvature of the catheter tip portion, said cooperating means comprising a helical groove defined on one of said body and collar sleeve and a user-movable member disposed on the other of said body and collar sleeve and carrying a tooth, said member being selectively movable between a first position in which said tooth is engaged with said helical groove to permit user-controlled rotative movement of the collar sleeve relatively about said body for effecting said relative longitudinal movement of the collar sleeve as said tooth travels engagedly along said helical groove and thereby enabling user-controlled fine adjustment of the catheter tip portion curvature by selective rotation of the collar sleeve about said body, and a second position of said member in which said tooth is disposed disengagedly remote from said helical groove to permit user-controlled nonrotative sliding movement of said collar sleeve longitudinally along said body for enabling user-controlled gross adjustment of the catheter tip portion curvature by selective nonrotative longitudinal sliding movement of the collar sleeve along said body, and said locking means further comprising return means for normally biasing said member toward said first position of the member in which said tooth engages said groove so as to prevent unintended relative longitudinal movement of said collar sleeve and body and thereby lock the catheter tip portion in a selected curvature.

16. The catheter handle of claim 15, further comprising resilient means attached to said body for urging the second mechanical coupling toward its initial position relative to the first mechanical coupling so as to return the catheter tip portion toward an initial, uncurved condition upon release of said locking means.

17. The catheter handle of claim 15, wherein said helical groove is oriented substantially transversely about a longitudinally-defined axis of said one of the body and collar sleeve.

18. The catheter handle of claim 15, wherein said helical groove is defined on said body and said member is disposed on said collar sleeve.

19. The catheter handle of claim 15, wherein said member comprises a pivotally-disposed lever carrying said tooth and pivotally movable for moving said tooth into and out of engagement with said helical groove.

20. The catheter handle of claim 19, wherein said lever comprises an elongated member carrying said tooth proximate one end of the elongated member, having a finger-engageable operating portion defined proximate an opposite end of the elongated member, and being pivotally movable about a fulcrum defined intermediate said one and opposite ends as user-controlled pressure is applied to and released from said finger-engageable operating portion.

21. The catheter handle of claim 15, wherein said helical groove is defined on said body, and wherein said member is movably disposed on said collar sleeve for disengagement of said tooth from a first portion of said helical groove and subsequent engagement of the tooth with a second portion of said helical groove as said collar sleeve is longitudinally moved nonrotatively along said body.

* * * * *